United States Patent
Yurusov

(10) Patent No.: US 11,303,846 B2
(45) Date of Patent: Apr. 12, 2022

(54) IMAGING SYSTEM AND METHOD CAPABLE OF PROCESSING MULTIPLE IMAGING FORMATS

(71) Applicant: MediCapture, Inc., Plymouth Meeting, PA (US)

(72) Inventor: Alexander Yurusov, New Taipei (TW)

(73) Assignee: MediCapture, Inc., Plymouth Meeting, PA (US)

( * ) Notice: Subject to any disclaimer, the term of this patent is extended or adjusted under 35 U.S.C. 154(b) by 0 days.

(21) Appl. No.: 16/770,047

(22) PCT Filed: Dec. 5, 2018

(86) PCT No.: PCT/US2018/064049
§ 371 (c)(1),
(2) Date: Jun. 4, 2020

(87) PCT Pub. No.: WO2019/113193
PCT Pub. Date: Jun. 13, 2019

(65) Prior Publication Data
US 2020/0351468 A1     Nov. 5, 2020

Related U.S. Application Data

(60) Provisional application No. 62/595,156, filed on Dec. 6, 2017.

(51) Int. Cl.
*H04N 7/01* (2006.01)
*G16H 30/20* (2018.01)
*G16H 30/40* (2018.01)

(52) U.S. Cl.
CPC ............ *H04N 7/013* (2013.01); *G16H 30/20* (2018.01); *G16H 30/40* (2018.01); *H04N 7/0125* (2013.01)

(58) Field of Classification Search
CPC .. H04N 13/139; H04N 7/013; H04N 21/4402; H04N 2201/33378;
(Continued)

(56) References Cited

U.S. PATENT DOCUMENTS 4,872,054 A * 10/1989 Gray ............... G09G 1/285
                                                    348/441
8,438,408 B2 * 5/2013 Louboutin ......... H04N 21/4126
                                                    713/320
(Continued)

FOREIGN PATENT DOCUMENTS

EP         3226551 A1    10/2017

OTHER PUBLICATIONS

"Installation and Operation Manal Blackmagic Converters", Black Magic Design, Jul. 1, 2015, 82 pp., http://documents.blackmagicdesign.com/Converters/2015-07-12/Blackmagic_Converters_Manual.pdf, Jan. 27, 2018.
(Continued)

*Primary Examiner* — Paulos M Natnael
(74) *Attorney, Agent, or Firm* — Kaplan Breyer Schwarz, LLP

(57) ABSTRACT

An digital imaging system and method that is provided that is capable of receiving and processing multiple types of image formats. Thus, the system is capable of receiving image signals from multiple types of image sources, such as medical imaging devices, that may each use different image formats, and converting the image format of the received image signals to the image formats required by one or more predetermined devices, such as an image recording device and a display.

23 Claims, 6 Drawing Sheets

(58) Field of Classification Search
CPC .......... H04N 7/0125; H04N 9/79; H04N 5/76; H04N 5/46; H04N 5/77; H04N 7/01; G16H 30/20; G16H 30/40; G09G 2340/125; G09G 2360/02; G09G 5/377; G09G 2354/00; G09G 2370/12; G09G 2370/20; G09G 2380/08; G09G 5/005
See application file for complete search history.

(56) References Cited

U.S. PATENT DOCUMENTS

| | | | | |
|---|---|---|---|---|
| 8,885,099 | B2* | 11/2014 | Balram | G11B 27/034 348/441 |
| 8,976,298 | B2* | 3/2015 | Turkington | H04N 5/213 348/607 |
| 9,237,296 | B2* | 1/2016 | Jung | H04N 5/44582 |
| 10,049,498 | B2* | 8/2018 | Li | H04N 21/43615 |
| 10,341,607 | B2* | 7/2019 | Komatsu | H04N 5/7491 |
| 10,638,105 | B2* | 4/2020 | Luo | G06F 3/1454 |
| 10,694,224 | B2* | 6/2020 | Kwon | H04N 21/812 |
| 2001/0019587 | A1 | 9/2001 | Hashimoto et al. | |
| 2003/0035065 | A1* | 2/2003 | Kim | H04N 9/642 348/558 |
| 2003/0184803 | A1* | 10/2003 | Yamada | H04N 1/3333 358/1.16 |
| 2003/0206242 | A1* | 11/2003 | Choi | H04N 9/641 348/441 |
| 2006/0285753 | A1* | 12/2006 | Yamasaki | G16H 30/20 382/209 |
| 2011/0102544 | A1* | 5/2011 | Kim | H04N 13/189 348/43 |
| 2011/0185204 | A1* | 7/2011 | Louboutin | H04N 21/4436 713/320 |
| 2012/0179670 | A1 | 7/2012 | Burke et al. | |
| 2012/0249736 | A1* | 10/2012 | Barrett | H04N 13/139 348/43 |
| 2013/0093844 | A1* | 4/2013 | Shuto | H04N 13/139 348/43 |
| 2014/0375768 | A1 | 12/2014 | Tsuchiya et al. | |
| 2015/0302146 | A1* | 10/2015 | Marshall | G06F 3/04817 345/173 |
| 2016/0094803 | A1* | 3/2016 | Possos | H04N 7/0112 348/448 |
| 2017/0221446 | A1 | 8/2017 | Yang et al. | |
| 2019/0191124 | A1* | 6/2019 | Peng | H04N 7/0125 |

OTHER PUBLICATIONS

Authorized Officer: Blaine R. Copenheaver, International Search Report and Written Opinion issued in counterpart PCT application No. PCT/US2018/064049, Mar. 4, 2019, 9 pp.
"Celestron Digitales LCD-Mikroskop II", Dec. 31, 2015, https://www.optik-pro.de/Produktownloads/54870_bedienungsanlei.pdf, May 20, 2021.
Extended European Search report issued in counterpart EP patent application No. 18885386.5, dated May 20, 2021, 9 pp.

* cited by examiner

IMAGING SYSTEM AND METHOD CAPABLE OF PROCESSING MULTIPLE IMAGING FORMATS

STATEMENT OF RELATED CASES

This application claims priority to U.S. Provisional Application Ser. No. 62/595,156, filed Dec. 6, 2017, whose entire disclosure is incorporated herein by reference.

FIELD OF THE INVENTION

The present invention relates to imaging systems and, more particularly, to an imaging system and method capable of receiving and processing multiple image formats.

BACKGROUND OF THE INVENTION

Medical imaging devices, such as endoscopic imaging devices, are commonly used during medical procedures. The images from such medical devices may be viewed in real time on displays/monitors during the medical procedure, may be recorded using an image recording device, may be archived and/or may be shared with others. Further, different types of medical imaging devices can utilize different image formats, such as an HDMI format, a DP (Display Port) format, an HD SDI format, a Quad SDI format, a 3G-SDI format, a 6G SDI format, a 12G SDI format, a 3D format, and a 4K format. Thus, there is a need for an imaging system that is capable of processing multiple input image formats and converting the input image formats into the formats and/or resolutions needed by other devices, such as image recording devices, image storage devices, etc.

SUMMARY OF THE INVENTION

An object of the present invention is to solve at least the above problems and/or disadvantages and to provide at least the advantages described hereinafter.

Another object of the present invention is to provide an imaging system that enables the display of an undistorted input image signal with no visible time delay via loop outputs, and that also coverts the input image signal for recording on an image recording device.

Another object of the present invention is to provide an imaging system that enables the display of an undistorted input image signal with no visible time delay via loop outputs, that also coverts the input image signal for recording on an image recording device, and that allows for the control and operation of the image recording device via user interface (UI) overlay.

Another object of the present invention is to provide an imaging system that provides multiple options to display and record single and complex image sources such as, for example, a 3D image source or a Quad image source for ultra high resolutions (4K).

Another object of the present invention is to provide an imaging system that provides multiple options to record an input image signal in commercial and medical image formats at the same time, eliminating the need for further image conversion after image recording or capture.

Another object of the present invention is to provide an imaging system that provides multiple options for simultaneous image recording in different image formats and different resolutions to suit various purposes, such as diagnostics or archiving.

The present invention provides an imaging system and method that is capable of receiving and processing multiple types of image formats. Thus, the system is capable of receiving image signals from multiple types of image sources, that may each use different image formats, and converting the image format of the received image signal to the image formats required by one or more predetermined devices.

In various embodiments, a conversion unit for use in an imaging system is disclosed. The conversion unit is configured to receive an image signal from one or more image sources, and to convert the image format of the received image signal to a predetermined image format configured for one or more predetermined devices, such as a display or video recording device (hereinafter "output device(s)). In some embodiments, the conversion unit outputs a converted image signal to a first output device at a first resolution and/or using a first CODEC and outputs second converted image signal to a second output device a second resolution and/or using a second CODEC. In some embodiments, a first output device includes at least one video recording device.

An embodiment of the invention is a system, comprising at least one output device, wherein the at least one output device is configured to receive and process image signals having at least one predetermined image format, and wherein the at least one output device comprises at least one image recording device for recording received image signals; and a conversion unit configured to receive an input image signal having an input image format, convert the input image format of the input image signal to the at least one predetermined image format and output the converted image signal to the at least one output device; wherein the input image format is different than the at least one predetermined image format.

Another embodiment of the invention is a medical imaging system, comprising an image recording device, wherein the image recording device is configured to receive and record image signals having at least one predetermined image format; and a conversion unit configured to receive an input image signal from a medical imaging device having an input image format, convert the input image format of the input image signal to the at least one predetermined image format and output the converted image signal to the image recording device; wherein the input image format is different than the at least one predetermined image format.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1:
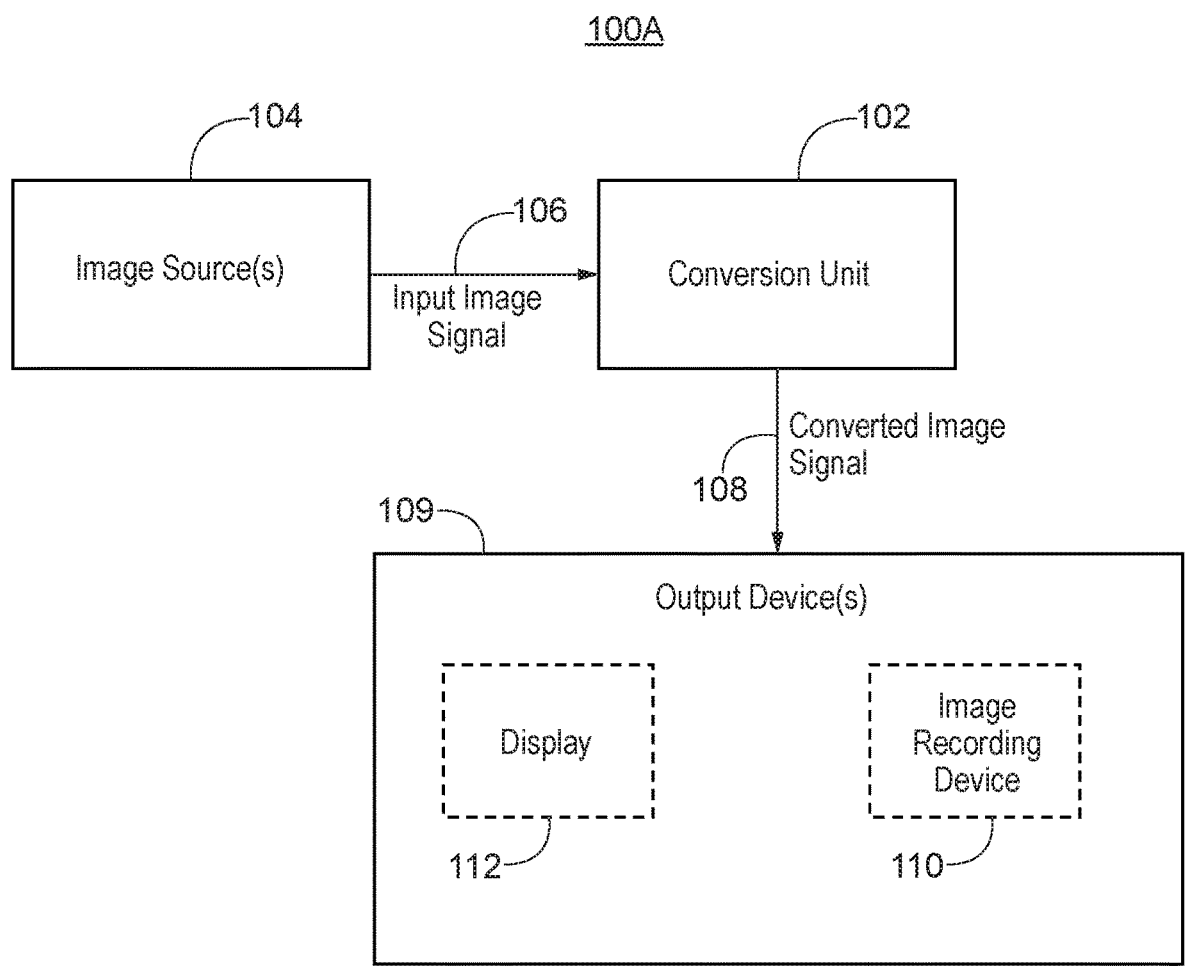
FIG. 1 is a block diagram of a digital imaging system, in accordance with an illustrative embodiment of the present invention.

In the following detailed description of various embodiments of the system and method of the present invention, numerous specific details are set forth in order to provide a thorough understanding of various aspects of one or more embodiments. However, the one or more embodiments may be practiced without some or all of these specific details. In other instances, well-known methods, procedures, and/or components have not been described in detail so as not to unnecessarily obscure aspects of embodiments.

Articles "a" and "an" are used herein to refer to one or to more than one (i.e. at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation.

Terms concerning electrical attachments, coupling and the like, such as "electrically connected," "electrically coupled," "signal connection," or "in signal communication" refer to a relationship wherein elements are electrically coupled to one another either directly or indirectly through intervening elements and through any combination of wired or wireless communication channels.

As used herein, the term "image" is used to refer to either still images or video. Thus, the phrase "image signal" refers to either a still image signal or a video signal, and the phrase "image recording device" refers to either a still image recording device or a video recording device. The phrases "image source(s)" and "imaging device(s)" are used interchangeably and refer to the source of an image signal such as, for example, a camera or a microscope.

While preferred embodiments are disclosed, still other embodiments of the system and method of the present invention will become apparent to those skilled in the art from the following detailed description, which shows and describes illustrative embodiments. As will be realized, the following disclosure is capable of modifications in various obvious aspects, all without departing from the spirit and scope of the present invention. Also, the reference or non-reference to a particular embodiment of the invention shall not be interpreted to limit the scope of the present invention.

The digital imaging systems and methods of the present invention are particularly suited for medical imaging applications, and some of the illustrative embodiments will be described in connection with medical imaging applications. However, it should be appreciated that the digital imaging systems and methods of the present invention can be used in other imaging applications.

FIG. 1 is a block diagram of a digital imaging system 100A, in accordance with an illustrative embodiment of the present invention. The system 100 includes a conversion unit 102 that is configured to receive an input image signal 106 from an image source 104. The conversion unit 102 is adapted to convert the image format of the input image signal 106 to an image format used by one or more output devices 109 and output the converted image signal 108. Examples image formats include, but are not limited to, an HDMI format, a DP (Display Port) format, an HD SDI format, a Quad SDI format, a 3G-SDI format, a 6G SDI format, a 12G SDI format, a 3D format, a 4K format, or any other image format known in the art. The converted image signal 108 output by the conversion unit 102 can collectively include more than one discreet converted image signals for more than one output device, with each discreet converted image signal having an image format used by a respective output device 109.

The conversion unit 102 can be configured such that the image format(s) of the converted image signal 108 is permanently set or, alternatively, such that the image format(s) of the converted image signal 108 can be selectively chosen by a user and/or automatically chosen by the conversion unit 102 based on types and/or number of input signal connections between the image source 104 and the conversion unit 102.

For example, the conversion unit 102 may be configured to automatically operate as: (1) a video pattern signal generator when no signal inputs from an image source 104 are connected; (2) a 4K HDMI or DP converter when four signal inputs are connected from the image source 104; (3) a 3D video converter when only two signal inputs are connected from the image source 104; (4) an SDI to HDMI or SDI to DP converter when the input image signal 106 provided to the conversion unit 102 is a single SDI signal via a single connection; and/or (5) any other predetermined configuration chosen based on the input image signal 106 and/or the connections between the image source 104 and the conversion unit 102.

In some illustrative embodiments, the type and/or location of the inputs to the conversion unit 102 can affect the image format conversion operation. For example, in some embodiments, when two input signal connections are provided, the conversion unit 102 can operate as a side-by-side and/or a top-bottom 3D convertor based on the position of the input signal connections in the conversion unit 102.

The output device(s) 109 can include one or more displays 112, one or more recording devices 110, and/or any other device that is adapted to receive and process image signals. In one illustrative embodiment, the output device(s) 109 includes at least one image recording device 110, and the image format of the converted image signal 108 output by the conversion unit 102 is preferably configured for archiving and review by the image recording device 110. Examples of image formats that are configured for archiving and review by the image recording device 110 include, but are not limited to, JPG still image, PNG still image, BMP still image, TIFF still image, TIFF multishot, DICOM still image, MPEG2 video, MPEG 4 H.264 video, MPEG 4 HEVC video, and DICOM video. In one illustrative embodiment, the converted image signal 108 includes an image signal for a first output device, such as a display 112, at a first resolution and/or using a first CODEC, and an image signal for a second output device, such as an image recording device 110, at a second resolution and/or using a second CODEC.

The image source 104 can include any imaging device known in the art, including, but not limited to, a surgical camera, an endoscopic imaging device, a biological imaging device (e.g., nuclear imaging, bioluminescence imaging, etc.), a microscopic imaging device (e.g., a microscope) and/or any other imaging device known in the art.

Figure 2:
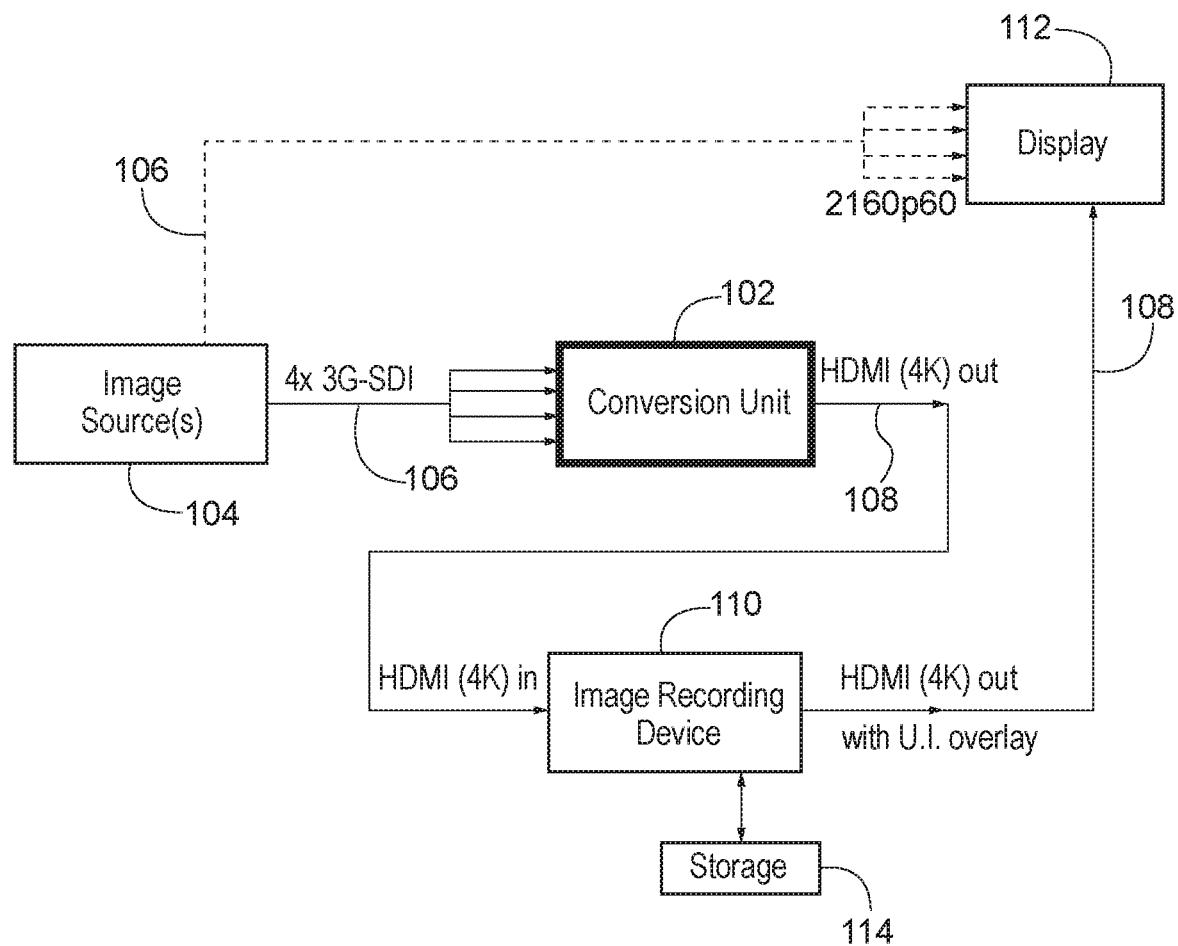
FIG. 2 is a block diagram of a digital imaging system, in accordance with another illustrative embodiment of the present invention

FIG. 2 is a block diagram of a digital imaging system 100B, in accordance with another illustrative embodiment of the present invention. In the embodiment of FIG. 2, the output device 109 is an image recording device 110. As discussed above in connection with the embodiment of FIG. 1, the input image signal 106 can be in any image format known in the art. However, for purposes of illustration, and as an example, the input image signal 106 in system 100B is a 4×3G-SDI signal (e.g., Quad SDI signal). As shown in FIG. 2, the input image signal 106 may optionally be simultaneously provided to the conversion unit 102 and a display 112. The display 112 can include any display known in the art, such as, for example, a monitor, a television, a projector, and/or any other display known in the art.

The conversion unit 102 is configured to receive the input image signal 106 from the image source 104, convert the image format of the input image signal 106 to an image format suitable for the image recording device 110 and output the converted image signal 108. In the example illustrated in FIG. 2, the image recording device 110 is capable of receiving an HDMI (4K) signal, and thus the conversion unit 102 outputs a converted image signal 108 in HDMI (4K) format.

In the embodiment of FIG. 2, the display 112 is preferably configured to display the input image signal 106 and/or the converted image signal 108. In the embodiment of FIG. 2, the image recording device 110 preferably outputs the input image signal 108, along with a user interface (UI) overlay, to the display 112. The UI overlaid on the converted image signal 108 can provide information to the user such as, for example, the status of the image recording device 110, the storage status with the amount of available free space or maximum available video recording time, the current date and time, the patient name and other patient details, and/or the status and resolution of the input image signal 106.

As discussed above, the present invention is particularly suited for implementing a medical imaging system. In a medical imaging system, the image source 104 is a medical imaging device and the display 112 can be configured to receive the converted image signal 108 and/or the input image signal 106 and display an image viewable by a surgeon and/or others during a medical procedure.

In the embodiment illustrated in FIG. 2, the image recording device 110 is coupled to and/or includes a storage unit 114. The storage unit 114 is configured to store the converted image signal 108. The storage unit 114 can include any machine-readable or computer-readable media capable of storing data, including, but not limited to, volatile memory, non-volatile memory, removable memory and/or non-removable memory. For example, memory may comprise read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), solid state storage, such as a USB storage device, a network-attached storage device, a cloud-based storage device and/or any other type of media suitable for storing information.

Figure 3:
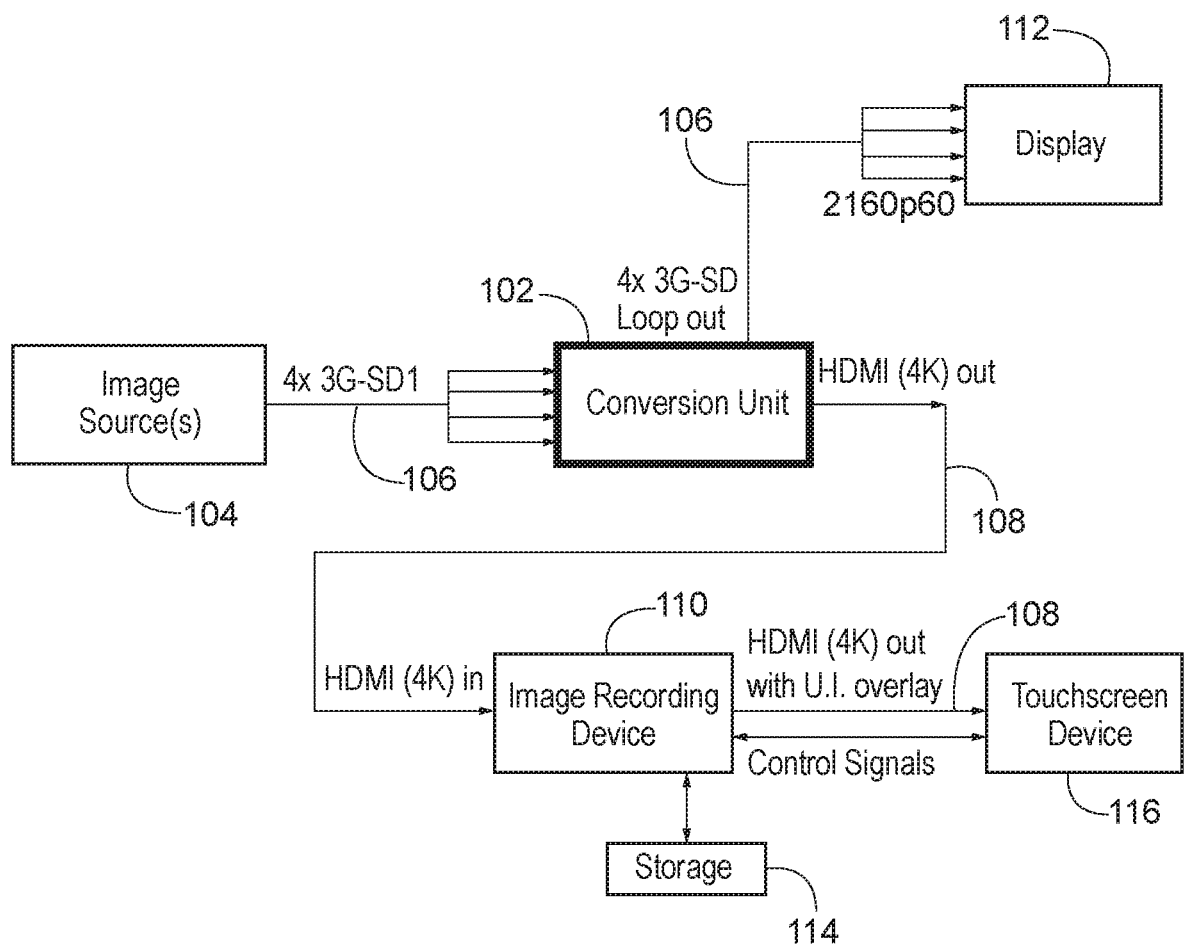
FIG. 3 is a block diagram of a digital imaging system, in accordance with another illustrative embodiment of the present invention.

FIG. 3 is a block diagram of a digital imaging system 100C, in accordance with another illustrative embodiment of the present invention. In the embodiment of FIG. 3, the output device 109 is an image recording device 110. As discussed above in connection with the embodiment of FIG. 1, the input image signal 106 can be in any image format known in the art. However, for purposes of illustration, and as an example, the input image signal 106 in system 100C is a 4×3G-SDI signal (e.g., Quad SDI signal). In the embodiment of FIG. 3, the input image signal 106 is also provided to the display 112 via an output on the conversion unit 102. As discussed above, the display 112 can include any display known in the art, such as, for example, a monitor, a television, a projector, and/or any other display known in the art.

The conversion unit 102 is configured to receive the input image signal 106 from the image source 104, convert the image format of the input image signal 106 to an image format suitable for the image recording device 110, and output the converted image signal 108. In the example illustrated in FIG. 3, the image recording device 110 is capable of receiving an HDMI (4K) signal, and thus the conversion unit 102 outputs a converted image signal 108 in HDMI (4K) format.

In the embodiment of FIG. 3, the image recording unit 110 is coupled to a touchscreen device 116. The touchscreen device 116 can be any type of touchscreen device known in the art such as, for example, a touchscreen display or a tablet computer. The touchscreen device 116 can be formed integrally with the image recording device 110, or can be a standalone device coupled to the image recording device 110.

The touchscreen device 116 may be configured to control the operation of the image recording device 110. Examples of image recording device operations that can be controlled by the touchscreen device 116 include, but are not limited to, starting/stopping recording, storage features, selecting input types, selecting output locations, and/or any other suitable control operations. In some embodiments, the touchscreen device 116 preferably utilizes a high-definition touchscreen. In some embodiments, the touchscreen device 116 is preferably configured to display the converted image signal 108, or a portion thereof, preferably with an overlaid graphical user interface image for enabling the image recording device control functions discussed above.

Figure 4:
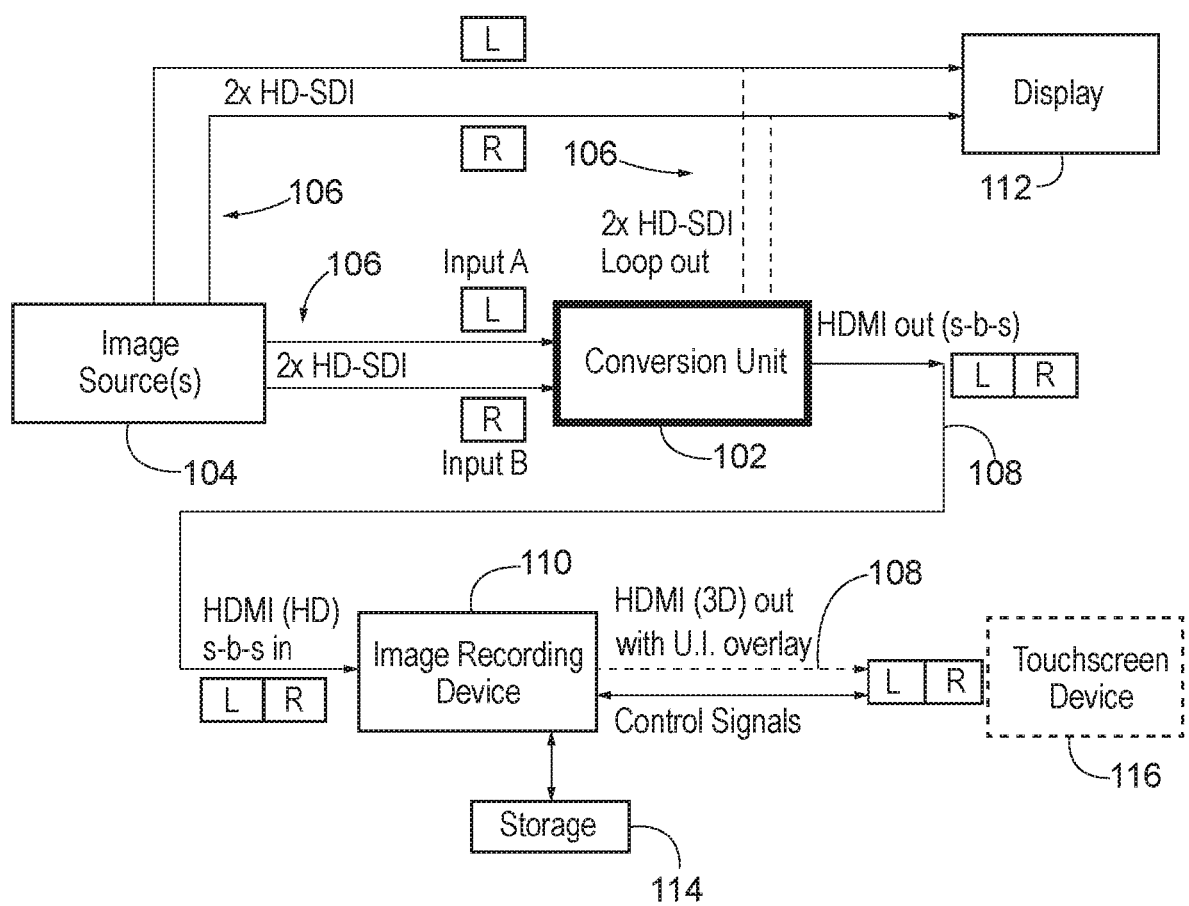
FIG. 4 is a block diagram of a digital imaging system, in accordance with another illustrative embodiment of the present invention.

FIG. 4 is a block diagram of a digital imaging system 100D, in accordance with another illustrative embodiment of the present invention. In the embodiment of FIG. 4, the output device 109 is an image recording device 110. As discussed above in connection with the embodiment of FIG. 1, the input image signal 106 can be in any image format known in the art. However, for purposes of illustration, and as an example, in the embodiment of FIG. 4, the input image signal 106 is a 3D signal and the conversion unit 102 is configured to convert the 3D formatted input image signal 106 to an 3D HDMI formatted converted image signal 108. The input image signal 106 can include any suitable 3D image signal, such as a 2×HD-SDI (1080p/i) or 2×3G SDI. The conversion unit 102 is configured to convert the 3D input image signal 106 to any suitable HDMI formatted converted image signal 108, such as a 1×HDMI side-by-side (1080p) signal, a 1×HDMI top-bottom (1080p) signal, a 1×HDMI Line-by-Line (1080p) signal, and/or a 1×HDMI Packed Frame (1080p) signal.

The input image signal 106 can be provided to the display 112 via either an output on the conversion unit 102 or directly from the image source 104. As in the embodiment of FIG. 3, the system 100D of FIG. 4 preferably includes a touchscreen device 116 for enabling the display and control functions described above in connection with the embodiment of FIG. 3.

Figure 5:
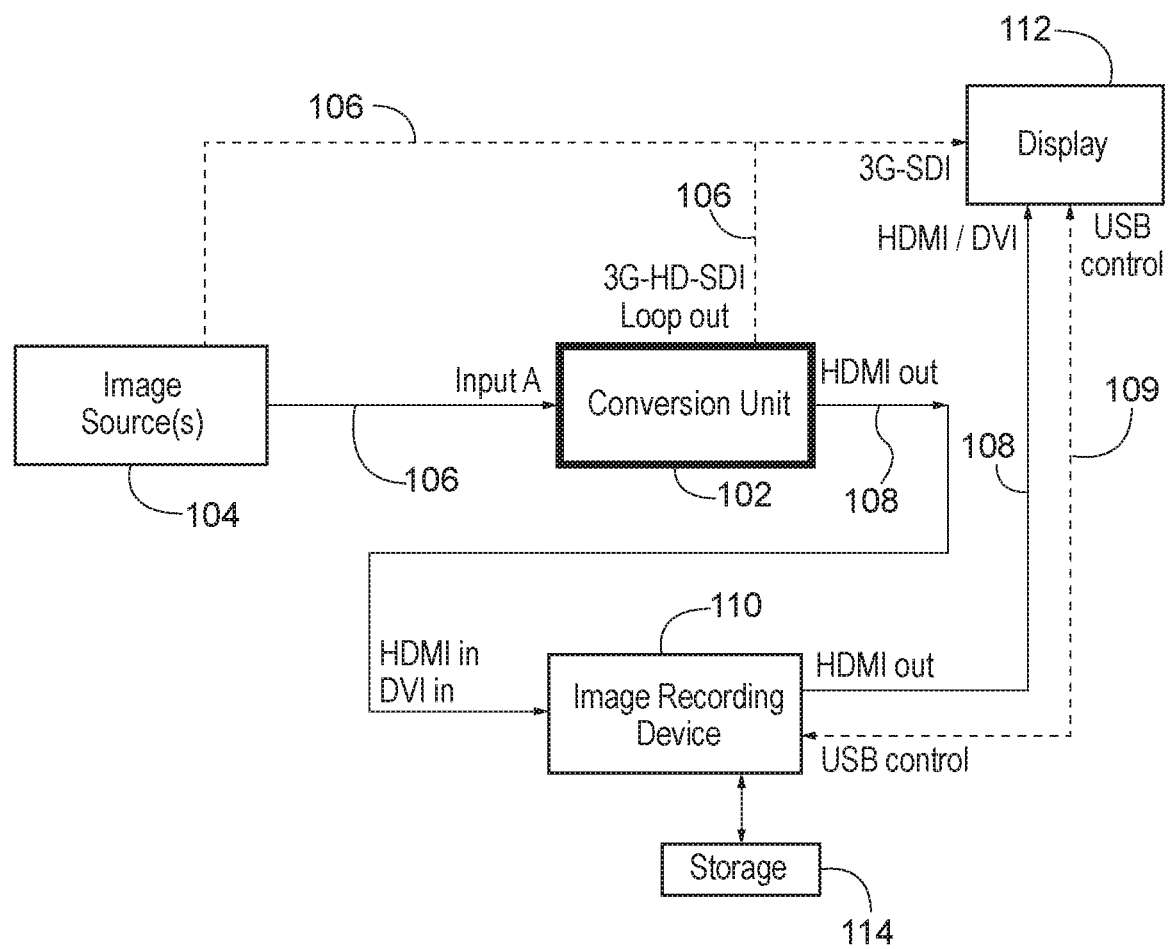
FIG. 5 is a block diagram of a digital imaging system, in accordance with another illustrative embodiment of the present invention.

FIG. 5 is a block diagram of a digital imaging system 100E, in accordance with another illustrative embodiment of the present invention. In the embodiment of FIG. 5, the output device 109 is an image recording device 110. As discussed above in connection with the embodiment of FIG. 1, the input image signal 106 can be in any image format known in the art. However, for purposes of illustration, and as an example, in the embodiment of FIG. 5, the input image signal 108 is a 1×SDI signal (e.g., a 1×3G-SDI signal, a 1×6G-SDI signal, a 1×12G-SDI signal, etc.) and the conversion unit 102 is configured to convert the 1×SDI signal to an HDMI formatted converted image signal 108. The input image signal 106 can include any suitable SDI signal, such as a 1080p SDI signal, a 2160p SDI signal, etc. The conversion unit 102 is configured to covert the 1×SDI signal to any suitable HDMI formatted converted image signal 108, such as an 1080p60 HDMI formatted signal, a 2160p30 HDMI formatted signal, a 2160p60 HDMI formatted signal, etc.

In the embodiment of FIG. 5, the display 112 is preferably configured to display the input image signal 106 and/or the converted image signal 108. As in the embodiment of FIG. 4, the input image signal 106 can be provided to the display 112 via either an output on the conversion unit 102 or directly from the image source 104. In the embodiment of FIG. 5, the image recording device 110 preferably outputs the converted image signal 108 to the display 112. In the embodiment of FIG. 5, the display 112 is preferably equipped with a touchscreen that enables control of the image recording device 110 via an interface 109 such as, for example, a USB interface.

Figure 6:
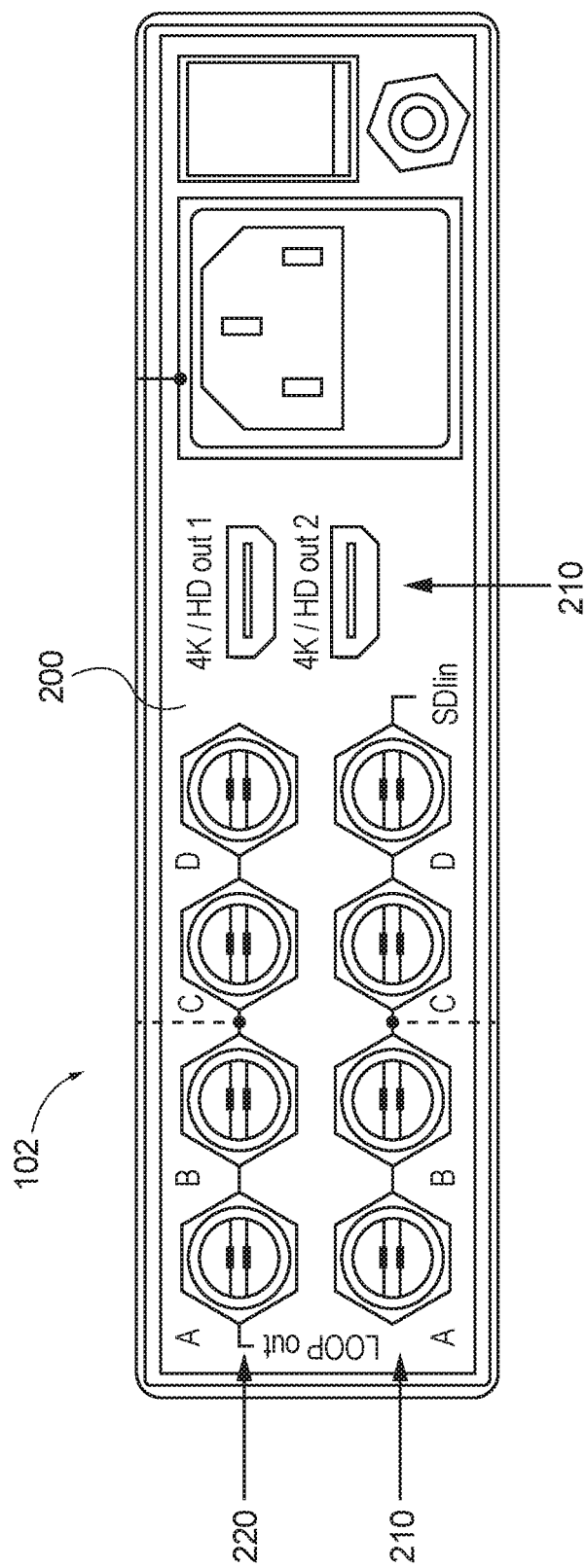
FIG. 6 is a schematic diagram of the input panel of a conversion unit, in accordance with another illustrative embodiment of the present invention.

FIG. 6 is a schematic diagram of the input panel 200 of an exemplary conversion unit 102, in accordance with an illustrative embodiment of the present invention. The panel 200 includes 4 input ports 210, individually labeled as "A," "B," "C" and "D." In the FIG. 6 embodiment, each of the input ports 210 is capable of receiving SD SDI, HD SDI, 3G SDI, 6G SDI and 12G SDI signals.

Corresponding loop output ports 220, each also individually labeled as "A," "B," "C" and "D" are provided for each of the input ports 210 for the purpose of providing original input image signals 106 to the display device 112. Thus, loop output ports "A," "B," "C," and "D" output the original input image signals 106 provided to input ports "A," "B," "C," and "D," respectively.

Input image signals 106 are processed and converted into the converted image signal 108 in HDMI or DP format. Two output ports 230, individually labeled "4K/HD out 1" and "4K/HD out 2" provide the HDMI or DP converted image signal 108. Both output ports 230 output the same signal, but possibly in different resolutions for matching the resolutions of the output devices, such as an image recording device 110 and a display 112.

The embodiment shown in FIG. 6 is one example of possible input and output ports. For example, although the two output ports 230 shown in FIG. 6 are adapted to provide HDMI or DP converted image signals 108, it should be appreciated that the two output ports 230 shown can be adapted to provide converted image signals 108 in other image formats and/or additional output ports 230 can be provided that are adapted to provide converted image signals 108 in other image formats. Similarly, the number of input ports 210 and the image formats they are adapted to receive, as well as the number of corresponding loop output ports 220, can be varied while still falling within the scope of the present invention.

The conversion unit 102 and the image recording device 110 described above in connection with FIGS. 1-6 can be implemented, in part, with one or more programs or applications run by one or more processors. The programs or applications that implement the conversion unit 102 and the image recording device 1100 are respective sets of computer readable instructions that are stored in memory that are accessed by the one or more processors.

The conversion unit 102 and/or the image recording device 110 described above in connection with FIGS. 1-6 can also be implemented using one or more low power and/or compact components. In some embodiments, the conversion unit 102 and/or the image recording device 110 include processor(s) and/or memory configured for low power/low physical space applications, such as processors and/or memory configured for mobile phone applications (e.g., handheld applications). Use of low power and compact components further allows the conversion unit 102 and/or the image recording device 110 to utilize smaller power supplies, providing a smaller foot print and reducing risk of fire, over supply, and/or other issues.

In some embodiments, the conversion unit 102 and the image recording device 110 each include a housing. The housing of the conversion unit 102 and the housing of the image recording device 110 are each preferably configured so as to allow a stacking configuration to reduce the footprint of the system.

The foregoing embodiments and advantages are merely exemplary, and are not to be construed as limiting the present invention. The description of the present invention is intended to be illustrative, and not to limit the scope of the claims. Many alternatives, modifications, and variations will be apparent to those skilled in the art. Various changes may be made without departing from the spirit and scope of the invention.

What is claimed is:

1. A system, comprising:
   at least one output device, wherein the at least one output device is configured to receive and process image signals having at least one predetermined image format, and wherein the at least one output device comprises at least one image recording device for recording received image signals; and
   a conversion unit configured to receive input image signals having different input image formats, automatically identify the input image format of a received input image signal, convert the input image format of the received input image signal to the at least one predetermined image format and output a converted image signal to the at least one output device, the conversion unit identifying the input image format of the received input signal based on types of input signal connections and/or the number of input signal connections;
   wherein the input image format of the received input signal is different than the at least one predetermined image format;
   wherein the at least one output device comprises the image recording device and a display; and
   wherein the conversion unit outputs the converted image signal to the display and the converted image signal to the image recording device, the converted image signal for the display having a resolution that matches a resolution of the display and the converted image signal for the image recording device having a resolution that matches a resolution of the image recording device.

2. The system of claim 1, wherein the input image format of the received input image signal comprises at least one of an HDMI format, a DP format, an HD SDI format, a Quad SDI format, a 3G-SDI format, a 6G SDI format, a 12G SDI format, a 3D format, and a 4K format.

3. The system of claim 1, wherein the input image format of the received input image signal comprises a Quad SDI format and the at least one predetermined image format comprises an HDMI or DP format.

4. The system of claim 1, wherein the input image format of the received input image signal comprises a 2×HD-SDI format and the at least one predetermined image format comprises an HDMI or DP format.

5. The system of claim 1, wherein the input image format of the received input image signal comprises a 1×SDI format and the at least one predetermined image format comprises an HDMI or DP format.

6. The system of claim 1, wherein the conversion unit outputs both the input image signal and the converted image signal to the display.

7. The system of claim 1, further comprising a storage unit coupled to the image recording device and configured to store the converted image signal.

8. The system of claim 7, wherein the storage unit comprises at least one of a USB storage device, a network-attached storage device and a cloud-based storage device.

9. The system of claim 1, further comprising a touchscreen device coupled to the image recording device, wherein the touchscreen device is configured to control an operation of the image recording device.

10. The system of claim 9, wherein the touchscreen device is configured to display at least a portion of the converted image signal and graphical user interface for controlling the operation of the image recording device.

11. The system of claim 9, wherein the touchscreen device is integrated with the image recording device.

12. The system of claim 1, further comprising at least one image source that generates the input image signals.

13. The system of claim 12, wherein the at least one image source comprises a medical imaging device.

14. The system of claim 13, wherein the medical imaging device comprises at least one of a surgical camera, an endoscopic imaging device, a biological imaging device, and a microscopic imaging device.

15. A medical imaging system, comprising:
an image recording device, wherein the image recording device is configured to receive and record image signals having at least one predetermined image format;
a conversion unit configured to receive input image signals from different medical imaging devices having different input image formats, automatically identify the input image format of a received image signal based on types of input signal connections and/or the number of input signal connections between the medical imaging device and the conversion unit, convert the input image format of the received input image signal to the at least one predetermined image format and output a converted image signal to the image recording device; and
a display, wherein the conversion unit outputs the converted image signal to the display and the converted image signal to the image recording device, the converted image signal for the display having a resolution that matches a resolution of the display and the converted image signal for the image recording device having a resolution that matches a resolution of the image recording device;
wherein the input image format of the received image signal is different than the at least one predetermined image format.

16. The system of claim 15, wherein the medical imaging devices comprise at least one of a surgical camera, an endoscopic imaging device, a biological imaging device, and a microscopic imaging device.

17. The system of claim 15, wherein the input image format of the received image signal comprises a Quad SDI format and the at least one predetermined image format comprises an HDMI or DP format.

18. The system of claim 15, wherein the input image format of the received image signal comprises a 2×HD-SDI format and the at least one predetermined image format comprises an HDMI or DP format.

19. The system of claim 15, wherein the input image format of the received image signal comprises a 1×SDI format and the at least one predetermined image format comprises an HDMI or DP format.

20. The system of claim 15, further comprising a touchscreen device coupled to the image recording device, wherein the touchscreen device is configured to control an operation of the image recording device.

21. The system of claim 20, wherein the touchscreen device is configured to display at least a portion of the converted image signal and graphical user interface for controlling the operation of the image recording device.

22. A system, comprising:
at least one output device, wherein the at least one output device is configured to receive and process image signals having at least one predetermined image format, and wherein the at least one output device comprises at least one image recording device for recording received image signals;
a conversion unit configured to receive input image signals having different input image formats, automatically identify the input image format of a received input image signal, convert the input image format of the received input image signal to the at least one predetermined image format and output a converted image signal to the at least one output device, the conversion unit identifying the input image format of the received input signal based on types of input signal connections and/or the number of input signal connections; and
a display, wherein the conversion unit includes at least one input port and at least one corresponding loop output port, the at least one input port receiving one of the input image signals and the at least one corresponding loop output port outputting the one of the input image signals to the display in its original image format;
wherein the input image format of the received input signal is different than the at least one predetermined image format.

23. A medical imaging system, comprising:
an image recording device, wherein the image recording device is configured to receive and record image signals having at least one predetermined image format;
a conversion unit configured to receive input image signals from different medical imaging devices having different input image formats, automatically identify the input image format of a received image signal based on types of input signal connections and/or the number of input signal connections between the medical imaging device and the conversion unit, convert the input image format of the received input image signal to the at least one predetermined image format and output a converted image signal to the image recording device; and a display, wherein the conversion unit includes at least one input port and at least one corresponding loop output port, the at least one input port receiving one of the input image signals and the at least one corresponding loop output port outputting the one of the input image signals to the display in its original image format;

wherein the input image format of the received image signal is different than the at least one predetermined image format.

* * * * *